(12) United States Patent
Model

(10) Patent No.: US 7,972,784 B2
(45) Date of Patent: Jul. 5, 2011

(54) METHOD FOR QUANTIFICATION OF METHYLATED DNA

(75) Inventor: Fabian Model, Seattle, WA (US)

(73) Assignee: Epigenomics AG, Berlin (DE)

(*) Notice: Subject to any disclaimer, the term of this patent is extended or adjusted under 35 U.S.C. 154(b) by 686 days.

(21) Appl. No.: 11/630,659

(22) PCT Filed: Jun. 23, 2005

(86) PCT No.: PCT/EP2005/006907
§ 371 (c)(1),
(2), (4) Date: Apr. 11, 2008

(87) PCT Pub. No.: WO2006/000447
PCT Pub. Date: Jan. 5, 2006

(65) Prior Publication Data
US 2008/0311566 A1    Dec. 18, 2008

(30) Foreign Application Priority Data
Jun. 23, 2004  (EP) ..................................... 04090255

(51) Int. Cl.
*C12Q 1/68* (2006.01)
*C12P 19/34* (2006.01)

(52) U.S. Cl. .......................................... 435/6; 435/91.2

(58) Field of Classification Search .............. 435/6, 91.2
See application file for complete search history.

(56) References Cited

U.S. PATENT DOCUMENTS

| | | | | |
|---|---|---|---|---|
| 6,331,393 B1 * | 12/2001 | Laird et al. | | 435/6 |
| 2003/0082600 A1 * | 5/2003 | Olek et al. | | 435/6 |
| 2005/0153316 A1 * | 7/2005 | Jeddeloh et al. | | 435/6 |
| 2005/0239101 A1 * | 10/2005 | Sukumar et al. | | 435/6 |
| 2005/0287553 A1 * | 12/2005 | Guetig et al. | | 435/6 |

OTHER PUBLICATIONS

Eads et al., Nucleic Acids Research 28(8) e32, 1-8 (2000).*
Rand et al., Methods 27, 114-120 (2002).*

* cited by examiner

*Primary Examiner* — Kenneth R. Horlick
(74) *Attorney, Agent, or Firm* — Kriegsman & Kriegsman

(57) ABSTRACT

The present invention relates to a method for the quantification of methylated cytosines in DNA. In the first step of the invention unmethylated cytosines in the DNA to be analysed are chemically converted into uracil while 5-methylcytosines remain unchanged. In a second step the converted DNA is amplified methylation specifically in a real time PCR using a methylation specific probe. Finally the amount of uniformly methylated DNA is calculated by combining criteria derived from the shape of the real time curve and from the signal intensity. The method is preferably used for diagnosis and/or prognosis of adverse events for individuals, for distinguishing cell types and tissues, or for investigating cell differentiation.

21 Claims, 4 Drawing Sheets

METHOD FOR QUANTIFICATION OF METHYLATED DNA

BACKGROUND OF THE INVENTION

Figure 1:
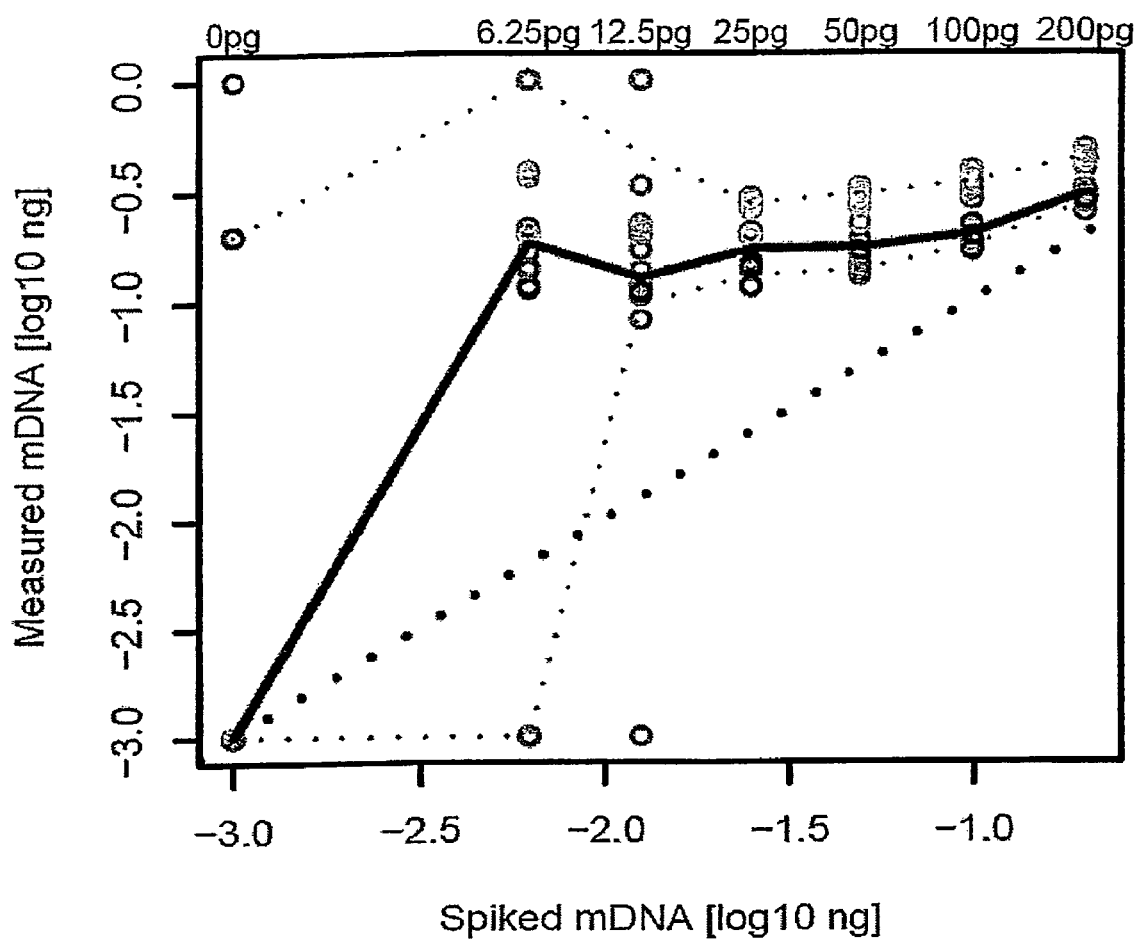

The present invention relates to a method for the quantification of methylated cytosines in DNA. 5-methylcytosine is the most frequent covalent base modification in the DNA of eukaryotic cells. It plays an important biological role, e.g. in the regulation of the transcription, in genetic imprinting, and in tumorigenesis (for review: Millar et al.: Five not four: History and significance of the fifth base. In: The Epigenome, S. Beck and A. Olek (eds.), Wiley-VCH Verlag Weinheim 2003, p. 3-20). Therefore, the identification of 5-methylcytosine as a component of genetic information is of considerable interest. However, a detection of 5-methylcytosine is difficult because 5-methylcytosine has the same base pairing behaviour as cytosine. Therefore the usual methods for identifying nucleic acids are not applicable. Moreover, the epigenetic information carried by 5-methylcytosine is completely lost during PCR amplification.

The usual methods for methylation analysis operate essentially according to two different principles. In the first case, methylation-specific restriction enzymes are utilized, and in the second case, a selective chemical conversion of unmethylated cytosines to uracil is conducted (bisulfite treatment; for review: European Patent Application 103 47 400.5, filing date: Oct. 9, 2003, applicant: Epigenomics AG). In a second step the enzymatically or chemically pretreated DNA is amplified and analyzed in different ways (for review: Fraga and Esteller: DNA methylation: a profile of methods and applications. Biotechniques, 2002 September; 33(3):632, 634, 636-49; WO 02/072880 pp. 1 ff). For sensitive detection the DNA is usually bisulfite treated and subsequently amplified by different Real Time PCR methods ("MethyLight"; for review: Trinh et al.: DNA methylation analysis by MethyLight technology. Methods. 2001 December; 25(4):456-62); WO00/70090; U.S. Pat. No. 6,331,393; Herman et al.: Methylation-specific PCR: a novel PCR assay for methylation status of CpG islands. Proc. Natl. Acad. Sci. USA. 1996 Sep 3; 93(18):9821-6; Cottrell et al.: A real-time PCR assay for DNA-methylation using methylation-specific blockers. Nucl. Acids. Res. 2004 32: e10).

A quantification of cytosine methylation is required for different applications, e.g. for classifications of tumors, for prognostic statements or for the prediction of drug effects. A particularly important application is the cancer diagnosis out of bodily fluids. Cancer cell DNA in bodily fluids has the property to be uniformly methylated over stretches of several 100 base pairs, while DNA of normal cells like blood shows a random mosaic methylation. However, a reliable diagnosis by detecting specially methylated cytosines in body fluids is difficult, because the aberrant methylation pattern has to be found within a large amount of background DNA, which is methylated differently, but which has the same base sequence. Therefore an optimal cancer test requires an exact quantification and a high specificity towards uniformly methylated DNA.

Several methods for quantification of methylation are known in the state of the art. These are usually based on a bisulfite treatment and a subsequent amplification. In most cases the analysis takes place after the amplification (e.g. Ms-SNuPE, hybridisation on microarrays, hybridisation in solution or direct bisulfite sequencing; for review: Fraga and Esteller 2002, loc. cit.). However, this "endpoint analysis" leads to several problems: due to product inhibition, enzyme instability and decrease of the reaction components the amplification does not proceed uniformly. Therefore a correlation between the amount of input DNA and the amount of amplificate does not always exist. As a consequence, the quantification is error-prone (for review: Kains: The PCR plateau phase—towards an understanding of its limitations. Biochem. Biophys. Acta 1494 (2000) 23-27).

The real time PCR based MethyLight technology uses a different approach for a quantification. This method analyses the exponential phase of the amplification instead of the endpoint. Traditionally a threshold cycle number (Ct) is calculated from the fluorescence signal that describes the exponential growth of the amplification (P S Bernard and C T Wittwer, Real-time PCR technology for cancer diagnostics, Clinical Chemistry 48, 2002). The Ct value is dependent on the starting amount of methylated DNA. By comparing the Ct value of an experimental sample with the Ct value of a standard curve the methylated DNA can be quantified (for review: Trinh et al. 2001, loc. cit.; Lehmann et al.: Quantitative assessment of promoter hypermethylation during breast cancer development. Am. J. Pathol. 2002 February; 160(2):605-12).

There are two commonly used methods to calculate the Ct value. The threshold method selects the cycle when the fluorescence signal exceeds the background fluorescence. The second derivative maximum method selects the cycle when the second derivative of the amplification curve has its maximum. For classical real-time PCR assays both methods produce identical results.

However, both methods do not produce exact results for the quantification of methylation via MethyLight assays. The MethyLight technology normally uses a methylation specific amplification (by methylation specific primers or blockers, sometimes methylation unspecific primers are used) combined with a methylation specific probe (for review: Trinh et al., 2001, loc. cit.). The methylation specific probe results in fluorescence signals from only a part of the generated amplificates depending on the methylation status of the CpG positions covered by the probe. This results in amplification curves that are downscaled compared to curves from completely methylated template DNA. These downscaled curves are the reason that both analysis methods generate incorrect results.

The threshold method assumes that all curves are in their exponential growth phase when exceeding the threshold. However, for samples with low proportions of DNA that is methylated at the probe (especially common in cancer diagnostics) this is not true. Amplification curves are already in the plateau phase and Ct estimation will be wrong.

The second derivative maximum method is independent from the overall intensity of the amplification curve. It only takes the shape into account which corresponds to a quantification of DNA that is methylated at the priming sites. The information generated by the methylation specific probe—represented by the signal intensity—is not used.

Here a new quantification method for uniformly methylated DNA is disclosed which leads to clearly improved results by combining both curve and intensity criteria. Due to the great importance of cytosine methylation and due to the above mentioned disadvantages in the prior art the present invention marks a significant technical progress.

DESCRIPTION

The present invention provides a novel method for the quantification of uniformly methylated cytosines in DNA. The invention is characterised in that the following steps are conducted:

a) a genomic DNA sample is chemically treated in such a way that all of the unmethylated cytosine bases are converted to uracil or another base which is dissimilar to cytosine in terms of base pairing behaviour, while the 5-methylcytosine bases remain unchanged, b) the chemically pretreated DNA is amplified in a real time PCR using at least one methylation specific probe and one methylation specific primer or blocker, c) the amount of DNA methylated at the primer/blocker binding site and the proportion of DNA methylated at the probe binding site in the amplificate are determined, d) the amount of uniformly methylated DNA is calculated by multiplying both values obtained in step c.

In the first step of the present invention a genomic DNA sample is chemically treated in such a way that all of the unmethylated cytosine bases are converted to uracil, or another base which is dissimilar to cytosine in terms of base pairing behaviour, while the 5-methylcytosine bases remain unchanged. It is also possible conduct the conversion of the DNA enzymatically. An enzyme which allows a methylation specific conversion was recently identified (see German patent application: 103 31 107.6, filing date: Jun. 4, 2003, applicant: Epigenomics AG). Depending on the diagnostic or scientific question to be analysed the genomic DNA sample can be obtained from various sources, e.g. from cell lines, biopsies or tissue embedded in paraffin. According to the above mentioned advantages it is particularly preferred to analyse bodily fluids like plasma, serum, stool or urine. The genomic DNA is isolated by standard methods, as found in references such as Sambrook, Fritsch and Maniatis, Molecular Cloning: A Laboratory Manual, CSH Press, 2nd edition, 1989: Isolation of genomic DNA from mammalian cells, Protocol I, p. 9.16-9.19 and in the commonly used QIAamp DNA mini kit protocol by Qiagen. The conversion of unmethylated, but not methylated, cytosine bases within the DNA sample is conducted with a converting agent, preferably a bisulfite such as disulfite or hydrogen sulfite. The reaction is performed according to standard procedures (e.g.: Frommer et al.: A genomic sequencing protocol that yields a positive display of 5-methylcytosine residues in individual DNA strands. Proc. Natl. Acad. Sci. USA. 1992 Mar. 1; 89(5):1827-31; Olek, A modified and improved method for bisulphite based cytosine methylation analysis. Nucleic Acids Res. 1996 Dec. 15; 24(24):5064-6; DE 100 29 915; DE 100 54 317). In a preferred embodiment, the conversion is conducted in presence of a reagent that denatures the DNA duplex and a radical scavenger (DE 100 29 915; German patent applications 10347397.1; 10347396.3; 10347400.5; 10347399.8; filing date: Oct. 9 2003, applicant: Epigenomics AG). It is also possible to conduct the conversion enzymatically, e.g by use of methylation specific cytidine deaminases (German patent application 103 31 107.6, filing date: Jul. 4, 2003, applicant: Epigenomics AG).

In the second step of the present invention the pretreated DNA is amplified methylation specifically by a real time PCR using a methylation specific probe. Several versions of methylation specific amplifications are known in the state of the art. In one embodiment methylation specific primers are used, i.e. primers which contain at least one CpG or one methylation specific TG or CA dinucleotide. The design of methylation specific primers and the PCR reaction conditions are known to a person skilled in the art ("MSP", Herman et al loc. cit. 1996; U.S. Pat. No. 6,331,393; Trinh et al 2001, loc. cit., all incorporated by reference). In another embodiment of the invention a methylation specific amplification is ensured by the use of non methylation specific primers in combination with methylation specific blocker oligonucleotides ("HEAVY METHYL"; WO 02/072880; Cottrell et al. loc cit. 2004; all incorporated by reference).

The amplification is conducted in the presence of a methylation specific real time probe, i.e. an oligomer which contains at least one CpG or one methylation specific TG or CA dinucleotide. Preferably the probe contains three methylation specific dinucleotides. Real time probe is defined here as a labelled probe which allows the detection of the amplificate during the amplification. Several versions of real time probes are known, e.g. hybridization (fluorescence energy transfer, aka "Lightcycler™" probes), hydrolysis (aka "Taqman™" probes), Scorpio, Sunrise, Molecular Beacon or Eclipse probes. Details concerning structure or detection of these probes are known in the state of the art (e.g. U.S. Pat. No. 6,331,393 with further references). For example hydrolysis (Taqman™) probes can be designed by the "PrimerExpress" Software (Applied Biosystems), and the "MGB Eclipse Design" Software by Epoch Biosciences can be used to design Eclipse probes.

In a preferred embodiment of the invention hybridization (LightCycler™) or hydrolysis (Taqman™) probes are used.

During the amplification the fluorescence signals are detected and plotted into a real time curve. Appropriate detection methods depend on the kind of probe used. Details are known by the person skilled in the art (e.g.: U.S. Pat. No. 6,331,393).

In the third step of the present invention the amount of DNA methylated at the primer/blocker binding site and the proportion of DNA methylated at the probe binding site within the amplificate are determined.

There are different ways to determine the amount of DNA methylated at the primer/blocker binding sites. It is reflected by the scaling invariant shape of the real time curve, which is independent of the proportion of generated amplificates that actually hybridize with detection probes. Several criteria describing the shape of the curve can be used for the calculation.

In a preferred embodiment a Ct value derived from a higher order derivative of the amplification curve serves as a criteria. Preferably the Ct value is calculated according to the second derivative maximum method by Wittwer et al. (U.S. Pat. No. 6,303,305, incorporated by reference). This method numerically computes the second derivative of the amplification curve, smoothes it with a spline fit and determines the Ct value as the maximum of the spline fit in cycle space. This Ct value is then used to compute the concentration of DNA methylated at the primer/blocker sites via the standard curve (P S Bernard and C T Wittwer, Real-time PCR technology for cancer diagnostics, Clinical Chemistry 48, 2002).

In a further preferred embodiment of the present invention the amount of methylated positions at the primer/blocker binding site is calculated by fitting a parametric model to the amplification curve. The amount of DNA that is methylated at the priming sites can then be estimated from the parameters for the slope of the model curve.

In a preferred embodiment for hydrolysis (Taqman™) probes a sigmoid function is used as a model according to Tichopad et al. (Improving quantitative real-time RT-PCR reproducibility by boosting primer-linked amplification efficiency. Biotechnology Letters 2002, Vol. 24, I 24, 2053-2056; incorporated by reference). In this case the parametric model is $f=y_0+a/(1+\exp((x_0-x)/b)$, where $y_0$ is the base fluorescence, a is the difference between $y_0$ and the maximum fluorescence, x is the actual cycle number, $x_0$ is the inflection point (first derivative maximum) and b is a parameter for the slope of the curve. The fit of this model can be done using most statistics packages (e.g. Splus). The concentration can then be estimated via a linear standard curve between the slope parameter b and the log concentration of the standard DNA. Parameters $y_0$ and a can also be used for the next step of determining the methylation proportion at the probe.

The third step of the present invention also comprises the determination of the proportion of DNA methylated at the probe binding site within the methylation specific amplificate. This proportion is reflected by the signal intensity of the methylation specific probe hybridizing to methylated and unmethylated DNA strands with different hybridization kinetics (J G Wetmur, Hybridization and renaturation kinetics of nucleic acids, Annual Reviews, 1976). Intensity criteria useful for the determination of the methylation proportion can be obtained in several ways.

In a preferred embodiment a linear interpolation between fluorescence intensities from the negative controls $y_0$ and the intensity of a completely methylated standard sample $y_1$ on each individual plate/carousel is conducted The proportion p is then given by the formula: $p=(y-y_0)/(y_1-y_0)$, wherein y is the intensity of the analyzed sample, $y_0$ is the intensity of the negative control and $y_1$ is the intensity of a completely methylated standard sample.

In a second preferred embodiment a global calibration of maximum and/or minimum intensity over several plates/carousels is performed, e.g. a linear interpolation between fluorescence intensities from the negative control $y_0$ and a completely methylated standard sample $y_1$ from one global calibration experiment for a certain assay. The proportion p is then calculated from the global calibration standards as $p=(y-y_0)/(y_1-y_0)$.

In a third preferred embodiment an additional probe that is specific for non-methylation (TG probe) is used in the assay and it's fluorescence intensity is monitored on a separate color channel. From the two intensity measurements ($y_{CG}$ from methylation specific CG probe and $y_{TG}$ from the non-methylation specific TG probe) the proportion p can be computed as $P=y_{CG}/(y_{CG}+y_{TG})$.

For each of these preferred embodiments the intensity can be calculated in different ways. Examples are last cycle, maximum intensity, intensity at root of any derivative or a parametric fit on the full amplification curve.

In a preferred embodiment y, $y_0$, $y_1$ or $y_{CG}$, $y_{TG}$ are computed as the maximum intensities of the respective amplification curves.

In a second preferred embodiment y, $y_0$, $y_1$ or $y_{CG}$, $y_{TG}$ are computed as the intensities in the cycle where the second derivative of the respective amplification curve is zero (inflection point). For some probe systems (e.g. hybridization (LightCycler™) probes) there might be several inflection points per amplification curve. In this case the intensity at the first inflection point is taken.

In a further preferred embodiment parameter a (the difference between $y_0$ and the maximum fluorescence) from the fitted model of step 3 is used to estimate y, $y_0$, $y_1$ or $y_{CG}$, $y_{TG}$.

In the fourth step of the present invention the amount of uniformly methylated amplificates (i.e. amplificates that are methylated at the CpG positions covered by the primer/blocker and at the CpG positions covered by the probe) is calculated by combining both values obtained in the third step. In a preferred embodiment the amount of uniformly methylated DNA $C_u$ is calculated by the product of the proportion of amplificates methylated at the probe p and the concentration of amplificates methylated at the primer/blocker $C_p$: $C_u=p*C_p$.

In a particularly preferred embodiment the amount of methylated positions at the primer/blocker binding site is calculated by the second derivative maximum method. The proportion is calculated by using negative control and completely methylated standard samples on each individual plate/carousel to linearly interpolate between minimum and maximum intensity. Intensities are estimated from the cycle where the respective amplification curve has its inflection point.

The methods disclosed here are preferably used for the diagnosis and/or prognosis of adverse events for patients or individuals, whereby these adverse events belong to at least one of the following categories: undesired drug interactions, cancer diseases, CNS malfunctions, damage or disease, symptoms of aggression or behavioral disturbances; clinical, psychological and social consequences of brain damage, psychotic disturbances and personality disorders, dementia and/or associated syndromes, cardiovascular disease, malfunction and damage, malfunction, damage or disease of the gastrointestinal tract, malfunction, damage or disease of the respiratory system, lesion, inflammation, infection, immunity and/or convalescence, malfunction, damage or disease of the body as an abnormality in the development process, malfunction, damage or disease of the skin, of the muscles, of the connective tissue or of the bones, endocrine and metabolic malfunction, damage or disease, headaches or sexual malfunction This new method also serves in a particularly preferred manner for distinguishing cell types and tissues or for investigating cell differentiation.

EXAMPLE 1

In this control experiment different amounts of artificially methylated DNA were spiked into a background of unmethylated sperm DNA and measured using a MSP MethyLight assay with hydrolysis (Tagman™) probes.

Uniformly methylated DNA was prepared via SSS1 treatment and the following amounts were spiked into 50 ng unmethylated sperm DNA: 200 pg, 100 pg, 50 pg, 25 pg, 12.5 pg, 6.25 pg, 0 pg. Three independent dilution series were pipetted and 6 repeated PCR reactions performed for every DNA concentration in every dilution series. Additionally each PCR run contained a 9 well standard curve of completely methylated DNA and 3 non-template controls.

Figure 2:
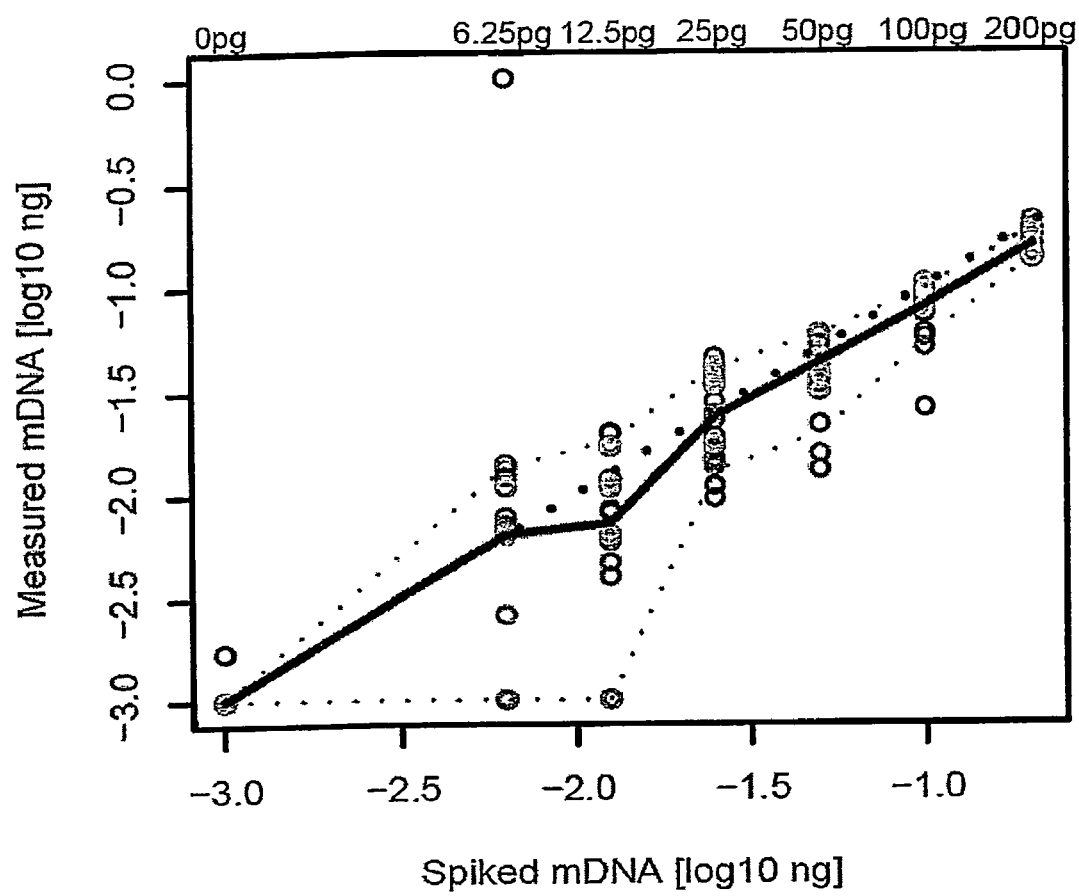

Data were analyzed using the standard $2^{nd}$ derivative method (column 2 in Table 1) and compared to estimates of uniformly methylated DNA using $2^{nd}$ derivative method with intensity correction (columns 3 and 4 in Table 1). The proportion of DNA methylated at the probe site was estimated by linear interpolation between the median NTC intensity and the median intensity of the completely methylated standards. The resulting calibration curves are shown in FIG. 1 and FIG. 2 respectively. Results of the standard $2^{nd}$ derivative method are heavily biased and over-estimate the amount of methylated DNA. Using the curve intensity to estimate the proportion of uniformly methylated DNA removes this bias and gives more correct measurement values.

Table 1: Numeric results of control experiment. The four columns are: amount of spiked uniformly methylated DNA in nanogram (Spiked mDNA), estimates for concentration of amplificates methylated at the primer/blocker (Measured mDNA $2^{nd}$ derivative), the proportion of amplificates methylated at the probe (Intensity Proportion) and the final total concentration of uniformly methylated amplificates (Measured mDNA corrected).

| Spiked mDNA [ng] | Measured mDNA 2nd derivative [ng] | Intensity Proportion | Measured mDNA corrected [ng] |
|---|---|---|---|
| 0.00E+00 | 0.00E+00 | 0.00E+00 | 0.00E+00 |
| 0.00E+00 | 2.00E−01 | 0.00E+00 | 0.00E+00 |
| 0.00E+00 | 2.00E−01 | 8.60E−03 | 1.72E−03 |
| 0.00E+00 | 0.00E+00 | 0.00E+00 | 0.00E+00 |
| 0.00E+00 | 0.00E+00 | 0.00E+00 | 0.00E+00 |
| 0.00E+00 | 0.00E+00 | 0.00E+00 | 0.00E+00 |
| 0.00E+00 | 2.00E−01 | 0.00E+00 | 0.00E+00 |
| 0.00E+00 | 1.22E+00 | 0.00E+00 | 0.00E+00 |
| 0.00E+00 | 2.79E−06 | 0.00E+00 | 0.00E+00 |
| 0.00E+00 | 0.00E+00 | 0.00E+00 | 0.00E+00 |
| 0.00E+00 | 0.00E+00 | 0.00E+00 | 0.00E+00 |
| 0.00E+00 | 0.00E+00 | 0.00E+00 | 0.00E+00 |
| 0.00E+00 | 0.00E+00 | 0.00E+00 | 0.00E+00 |
| 0.00E+00 | 0.00E+00 | 0.00E+00 | 0.00E+00 |
| 0.00E+00 | 0.00E+00 | 0.00E+00 | 0.00E+00 |
| 0.00E+00 | 0.00E+00 | 0.00E+00 | 0.00E+00 |
| 0.00E+00 | 0.00E+00 | 0.00E+00 | 0.00E+00 |
| 6.25E−03 | 1.38E−01 | 1.01E−01 | 1.40E−02 |
| 6.25E−03 | 1.17E−01 | 6.02E−02 | 7.05E−03 |
| 6.25E−03 | 6.53E+03 | 6.93E−03 | 4.52E+01 |
| 6.25E−03 | 1.74E+02 | 0.00E+00 | 0.00E+00 |
| 6.25E−03 | 1.41E−01 | 5.46E−02 | 7.69E−03 |
| 6.25E−03 | 1.69E−01 | 3.72E−02 | 6.27E−03 |
| 6.25E−03 | 2.16E−01 | 3.11E−02 | 6.73E−03 |
| 6.25E−03 | 1.42E−01 | 9.26E−02 | 1.32E−02 |
| 6.25E−03 | 2.00E−01 | 0.00E+00 | 0.00E+00 |
| 6.25E−03 | 1.13E−01 | 1.07E−01 | 1.21E−02 |
| 6.25E−03 | 2.00E−01 | 4.26E−03 | 8.51E−04 |
| 6.25E−03 | 0.00E+00 | 0.00E+00 | 0.00E+00 |
| 6.25E−03 | 0.00E+00 | 0.00E+00 | 0.00E+00 |
| 6.25E−03 | 3.88E−01 | 2.78E−02 | 1.08E−02 |
| 6.25E−03 | 0.00E+00 | 0.00E+00 | 0.00E+00 |
| 6.25E−03 | 3.67E−01 | 1.74E−02 | 6.36E−03 |
| 6.25E−03 | 8.48E+00 | 0.00E+00 | 0.00E+00 |
| 6.25E−03 | 2.00E−01 | 1.29E−02 | 2.58E−03 |
| 1.25E−02 | 1.15E−01 | 7.03E−02 | 8.07E−03 |
| 1.25E−02 | 1.12E−01 | 1.75E−01 | 1.96E−02 |
| 1.25E−02 | 1.08E−01 | 1.09E−01 | 1.17E−02 |
| 1.25E−02 | 1.04E−01 | 1.66E−01 | 1.73E−02 |
| 1.25E−02 | 8.20E−02 | 0.00E+00 | 0.00E+00 |
| 1.25E−02 | 1.19E−01 | 5.19E−02 | 6.15E−03 |
| 1.25E−02 | 1.37E−01 | 3.38E−02 | 4.63E−03 |
| 1.25E−02 | 1.71E−01 | 3.27E−03 | 5.59E−04 |
| 1.25E−02 | 2.01E−01 | 2.91E−02 | 5.84E−03 |
| 1.25E−02 | 5.39E+00 | 1.55E−03 | 8.34E−03 |
| 1.25E−02 | 1.08E−01 | 1.82E−01 | 1.98E−02 |
| 1.25E−02 | 1.11E−01 | 3.57E−02 | 3.95E−03 |
| 1.25E−02 | 1.40E+00 | 4.53E−03 | 6.33E−03 |
| 1.25E−02 | 0.00E+00 | 0.00E+00 | 0.00E+00 |
| 1.25E−02 | 2.24E−01 | 7.45E−02 | 1.67E−02 |
| 1.25E−02 | 3.35E−01 | 3.18E−02 | 1.06E−02 |
| 1.25E−02 | 2.15E−01 | 5.23E−02 | 1.13E−02 |
| 1.25E−02 | 2.00E−01 | 0.00E+00 | 0.00E+00 |
| 2.50E−02 | 1.47E−01 | 3.09E−01 | 4.55E−02 |
| 2.50E−02 | 1.52E−01 | 2.18E−01 | 3.32E−02 |
| 2.50E−02 | 1.47E−01 | 9.89E−02 | 1.46E−02 |
| 2.50E−02 | 1.41E−01 | 1.97E−01 | 2.78E−02 |
| 2.50E−02 | 1.15E−01 | 2.10E−01 | 2.42E−02 |
| 2.50E−02 | 1.37E−01 | 1.22E−01 | 1.66E−02 |
| 2.50E−02 | 1.95E−01 | 7.27E−02 | 1.42E−02 |
| 2.50E−02 | 2.06E−01 | 6.55E−02 | 1.35E−02 |
| 2.50E−02 | 2.08E−01 | 1.09E−01 | 2.27E−02 |
| 2.50E−02 | 1.42E−01 | 1.33E−01 | 1.89E−02 |
| 2.50E−02 | 1.42E−01 | 7.67E−02 | 1.09E−02 |
| 2.50E−02 | 1.17E−01 | 8.10E−02 | 9.49E−03 |
| 2.50E−02 | 2.79E−01 | 6.27E−02 | 1.75E−02 |
| 2.50E−02 | 1.95E−01 | 1.80E−01 | 3.52E−02 |
| 2.50E−02 | 2.98E−01 | 1.27E−01 | 3.77E−02 |
| 2.50E−02 | 2.62E−01 | 1.53E−01 | 4.01E−02 |
| 2.50E−02 | 2.62E−01 | 1.57E−01 | 4.11E−02 |
| 2.50E−02 | 2.79E−01 | 1.22E−01 | 3.40E−02 |
| 5.00E−02 | 1.36E−01 | 3.40E−01 | 4.62E−02 |
| 5.00E−02 | 1.63E−01 | 3.63E−01 | 5.91E−02 |
| 5.00E−02 | 1.39E−01 | 9.32E−02 | 1.30E−02 |
| 5.00E−02 | 1.30E−01 | 1.66E−01 | 2.15E−02 |
| 5.00E−02 | 1.40E−01 | 2.23E−01 | 3.11E−02 |
| 5.00E−02 | 1.48E−01 | 3.02E−01 | 4.46E−02 |
| 5.00E−02 | 1.81E−01 | 1.86E−01 | 3.37E−02 |
| 5.00E−02 | 1.49E−01 | 1.04E−01 | 1.55E−02 |
| 5.00E−02 | 1.85E−01 | 3.21E−01 | 5.93E−02 |
| 5.00E−02 | 1.90E−01 | 2.75E−01 | 5.24E−02 |
| 5.00E−02 | 1.69E−01 | 2.16E−01 | 3.65E−02 |
| 5.00E−02 | 1.70E−01 | 2.49E−01 | 4.24E−02 |
| 5.00E−02 | 2.24E−01 | 1.38E−01 | 3.09E−02 |
| 5.00E−02 | 2.68E−01 | 1.64E−01 | 4.40E−02 |
| 5.00E−02 | 2.79E−01 | 2.09E−01 | 5.83E−02 |
| 5.00E−02 | 3.10E−01 | 1.47E−01 | 4.56E−02 |
| 5.00E−02 | 3.05E−01 | 1.48E−01 | 4.52E−02 |
| 5.00E−02 | 3.31E−01 | 1.14E−01 | 3.78E−02 |
| 1.00E−01 | 1.76E−01 | 3.39E−01 | 5.96E−02 |
| 1.00E−01 | 1.97E−01 | 3.71E−01 | 7.31E−02 |
| 1.00E−01 | 1.97E−01 | 4.90E−01 | 9.64E−02 |
| 1.00E−01 | 1.79E−01 | 4.17E−01 | 7.48E−02 |
| 1.00E−01 | 1.97E−01 | 4.96E−01 | 9.79E−02 |
| 1.00E−01 | 1.86E−01 | 4.44E−01 | 8.27E−02 |
| 1.00E−01 | 2.02E−01 | 3.84E−01 | 7.78E−02 |
| 1.00E−01 | 2.01E−01 | 2.53E−01 | 5.08E−02 |
| 1.00E−01 | 2.14E−01 | 4.54E−01 | 9.72E−02 |
| 1.00E−01 | 2.24E−01 | 3.35E−01 | 7.51E−02 |
| 1.00E−01 | 1.96E−01 | 1.31E−01 | 2.57E−02 |
| 1.00E−01 | 1.69E−01 | 3.33E−01 | 5.65E−02 |
| 1.00E−01 | 3.12E−01 | 3.32E−01 | 1.04E−01 |
| 1.00E−01 | 2.88E−01 | 3.26E−01 | 9.37E−02 |
| 1.00E−01 | 3.21E−01 | 2.84E−01 | 9.12E−02 |
| 1.00E−01 | 3.45E−01 | 2.25E−01 | 7.78E−02 |
| 1.00E−01 | 3.55E−01 | 2.36E−01 | 8.37E−02 |
| 1.00E−01 | 3.94E−01 | 2.11E−01 | 8.32E−02 |
| 2.00E−01 | 3.09E−01 | 5.59E−01 | 1.73E−01 |
| 2.00E−01 | 2.89E−01 | 4.95E−01 | 1.43E−01 |
| 2.00E−01 | 2.53E−01 | 5.39E−01 | 1.36E−01 |
| 2.00E−01 | 2.78B−01 | 5.74E−01 | 1.60E−01 |
| 2.00E−01 | 3.06E−01 | 6.09E−01 | 1.86E−01 |
| 2.00E−01 | 3.25E−01 | 5.39E−01 | 1.75E−01 |
| 2.00E−01 | 2.84E−01 | 4.89E−01 | 1.39E−01 |
| 2.00E−01 | 2.90E−01 | 4.62E−01 | 1.34E−01 |
| 2.00E−01 | 4.02E−01 | 3.95E−01 | 1.59E−01 |
| 2.00E−01 | 4.39E−01 | 4.68E−01 | 2.05E−01 |
| 2.00E−01 | 4.91E−01 | 3.84E−01 | 1.88E−01 |
| 2.00E−01 | 4.50E−01 | 3.07E−01 | 1.38E−01 |

EXAMPLE 2

In this experiment 1.8 mL serum samples from 30 patients without colon cancer and 30 patients with colon cancer or colon polyps were measured using a MSP MethyLight assay with hydrolysis (Taqman™) probes. The aim is to predict the presence of colon cancer with high sensitivity and specificity. The area under the ROC curve (AUC) is used to quantify the prediction performance. A Receiver Operating Characteristic (ROC) curve is a plot of the true positive rate against the false positive rate for the different possible cutpoints of a diagnostic test. It shows the tradeoff between sensitivity and specificity depending on the selected cutpoint (any increase in sensitivity will be accompanied by a decrease in specificity). The area under an ROC curve (AUC) is a measure for the accuracy of a diagnostic test (the larger the area the better, optimum is 1, a random test would have a ROC curve lying on the diagonal with an area of 0.5; for reference: J. P. Egan. Signal Detection Theory and ROC Analysis, Academic Press, New York, 1975).

Figure 3:
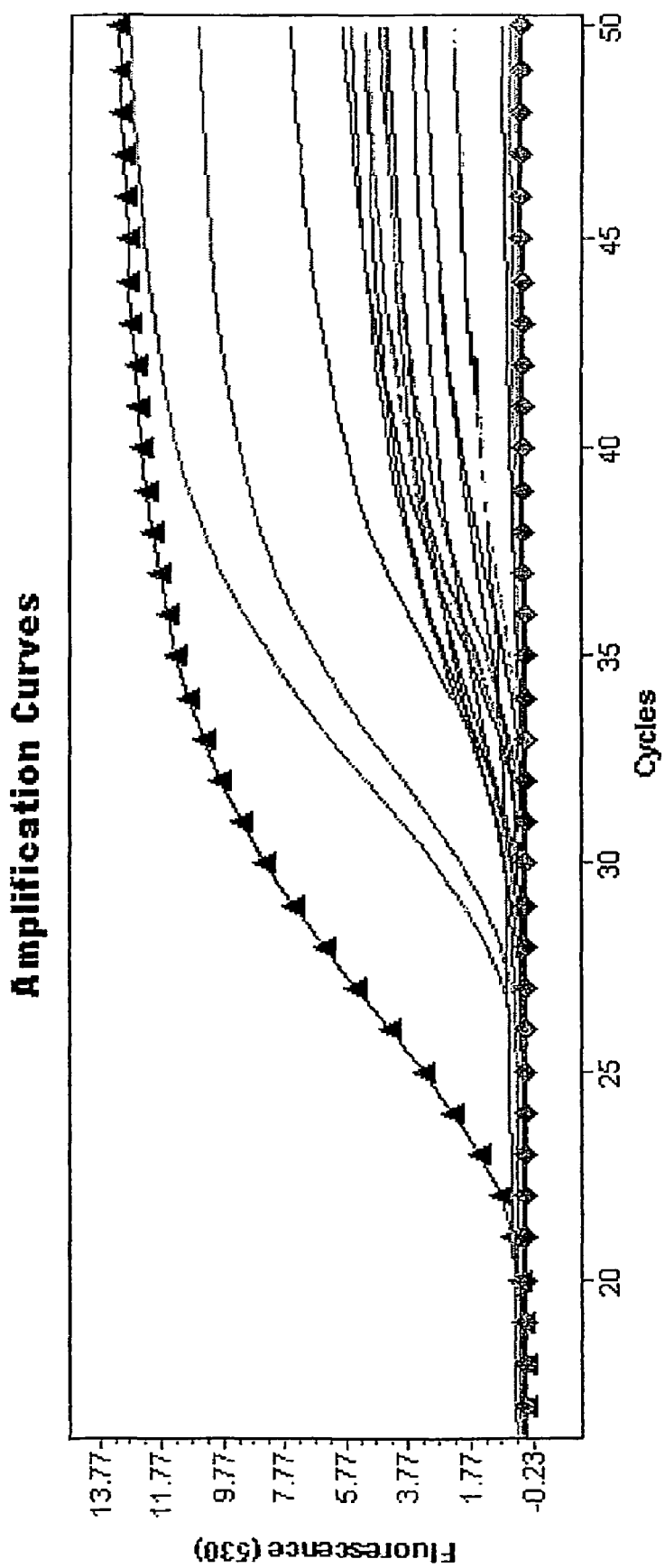
Figure 4:
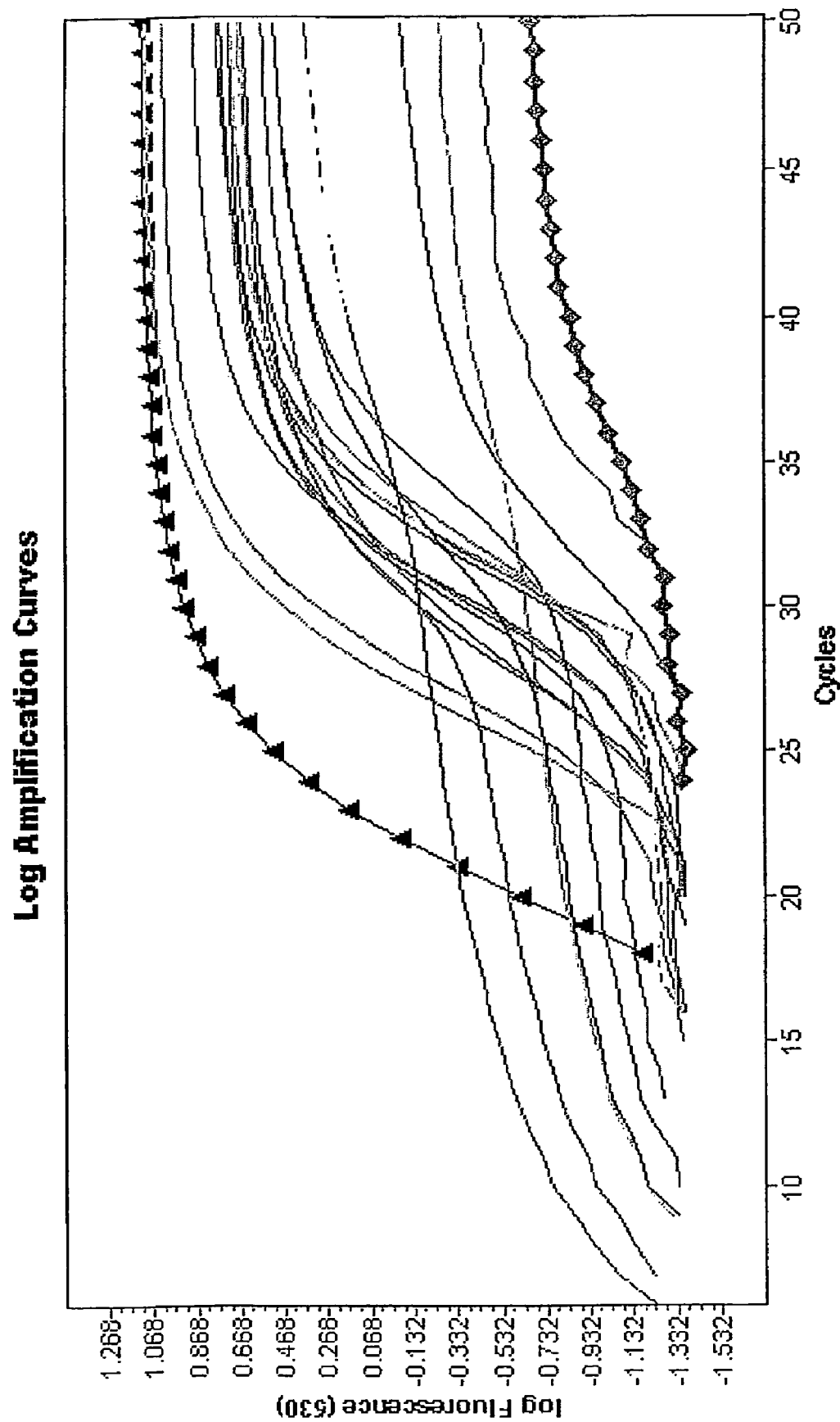

FIG. 3 and FIG. 4 show amplification curves of 20 of the colon cancer serum samples. All samples show some degree of amplification. However, absolute intensities of the amplification curves are anywhere in between the intensity of the negative control and the positive control.

Table 2 shows the computed values for the concentration of amplificates methylated at the primer sites, proportion of amplificates methylated at the probe site and resulting concentration of uniformly methylated amplificates relative to the total amount of bisulphite DNA from the respective sample.

The amount of amplificates methylated at the primer/blocker binding site was calculated by the second derivative maximum method. The proportion was calculated by using negative control and standard samples on each individual plate/carousel. Intensities were estimated from the maximum intensities of the respective amplification curves.

Using only the DNA concentrations estimated by the second derivative maximum method the prediction performance is AUC=0.83. Using DNA concentrations estimated by the classical threshold method prediction performance is AUC=0.89. The method disclosed in the present invention achieves a prediction performance of AUC=0.95.

Table 2: Estimates for concentration of amplificates methylated at the primer/blocker (pgDNA) and the proportion of amplificates methylated at the probe (IntensityProportion). The final total concentration of uniformly methylated amplificates (totalConc) is normalized to the total amount of bisulphite DNA in the patient sample (pg bisDNA).

| Sample ID | Cp | pg DNA | pg Bis-DNA | rel Conc (pgDNA/pgBisDNA) | Intensity Proportion | total Conc (IntensityProportion*relConc) | C > 0.0001 Call |
|---|---|---|---|---|---|---|---|
| C1 | 31.45 | 86.096 | 29600 | 2.91E-003 | 0.34788732 | 1.01E-003 | TRUE |
| C10 | 29.34 | 376.490389 | 250000 | 1.51E-003 | 0.41895636 | 6.31E-004 | TRUE |
| C11 | 27.21 | 1669.55272 | 39000 | 4.28E-002 | 0.79122604 | 3.39E-002 | TRUE |
| C12 | 27.67 | 1210.33514 | 15780 | 7.67E-002 | 0.27009928 | 2.07E-002 | TRUE |
| C13 | 19.87 | 282903.534 | 994000 | 2.85E-001 | 1 | 2.85E-001 | TRUE |
| C14 | 30.97 | 120.434105 | 25600 | 4.70E-003 | 0.38344493 | 1.80E-003 | TRUE |
| C15 | 27.56 | 1307.10612 | 84000 | 1.56E-002 | 0.33082429 | 5.15E-003 | TRUE |
| C16 | 31.15 | 106.190686 | 28000 | 3.79E-003 | 0.01179866 | 4.47E-005 | FALSE |
| C17 | 26.7 | 2384.94747 | 78800 | 3.03E-002 | 0.95714615 | 2.90E-002 | TRUE |
| C18 | 31.7 | 72.2870335 | 77800 | 9.29E-004 | 0.15952435 | 1.48E-004 | TRUE |
| C19 | 30.92 | 124.719303 | 104200 | 1.20E-003 | 0.37986608 | 4.55E-004 | TRUE |
| C2 | 30.06 | 227.562996 | 66600 | 3.42E-003 | 0.56899099 | 1.94E-003 | TRUE |
| C20 | 30.53 | 163.821278 | 17580 | 9.32E-003 | 0.23807434 | 2.22E-003 | TRUE |
| C21 | 32.89 | 60.5617866 | 65400 | 9.26E-004 | 0.54843472 | 5.08E-004 | TRUE |
| C22 | 32.46 | 80.7895379 | 25000 | 3.23E-003 | 0.39946076 | 1.29E-003 | TRUE |
| C23 | 31.1 | 201.001253 | 107600 | 1.87E-003 | 0.19684163 | 3.68E-004 | TRUE |
| C24 | 30.04 | 409.000611 | 32000 | 1.28E-002 | 0.03900883 | 4.99E-004 | TRUE |
| C25 | 35.59 | 9.91591111 | 15340 | 6.46E-004 | 0.07155543 | 4.63E-005 | FALSE |
| C26 | 23.06 | 43987.9007 | 300000 | 1.47E-001 | 1 | 1.47E-001 | TRUE |
| C27 | 31.18 | 190.508275 | 125600 | 1.52E-003 | 0.09541437 | 1.45E-004 | TRUE |
| C28 | 32.37 | 85.8125206 | 64200 | 1.34E-003 | 0.75220936 | 1.01E-003 | TRUE |
| C29 | 34.3 | 23.5397562 | 17040 | 1.38E-003 | 0.69432734 | 9.59E-004 | TRUE |
| C3 | 29.16 | 426.989266 | 189800 | 2.25E-003 | 0.38309859 | 8.62E-004 | TRUE |
| C30 | 31.38 | 166.610184 | 71800 | 2.32E-003 | 0.47859114 | 1.11E-003 | TRUE |
| C4 | 29.06 | 457.915480 | 54200 | 8.45E-003 | 0.33398753 | 2.82E-003 | TRUE |
| C5 | 32.5 | 41.3155421 | 25200 | 1.64E-003 | 0.02724544 | 4.47E-005 | FALSE |
| C6 | 32.32 | 46.8572200 | 55800 | 8.40E-004 | 0.23419533 | 1.97E-004 | TRUE |
| C7 | 30.82 | 133.752541 | 51600 | 2.59E-003 | 0.44054490 | 1.14E-003 | TRUE |
| C8 | 29.92 | 250.967427 | 18900 | 1.33E-002 | 0.0483722 | 6.42E-004 | TRUE |
| C9 | 33.35 | 22.8024927 | 13300 | 1.71E-003 | 0.16430385 | 2.82E-004 | TRUE |
| N1 | 32.87 | 61.3790141 | 304000 | 2.02E-004 | 0.01215415 | 2.45E-006 | FALSE |
| N10 | 32.07 | 104.922615 | 31600 | 3.32E-005 | 0.00256777 | 8.53E-006 | FALSE |
| N11 | 32.96 | 30.2583342 | 49200 | 6.15E-004 | 0.13163193 | 8.10E-005 | FALSE |
| N12 | 34.08 | 13.1542029 | 46200 | 2.85E-004 | 0.60629120 | 1.73E-004 | TRUE |
| N13 | 31.35 | 100.208474 | 32000 | 3.13E-003 | 0.01674544 | 5.24E-005 | FALSE |
| N14 | 29.19 | 499.601739 | 140800 | 3.55E-003 | 0.00597748 | 2.12E-005 | FALSE |
| N15 | 55 | 2.29891E-0 | 250000 | 9.20E-012 | 0 | 0.00E+001 | FALSE |
| N16 | 25.96 | 5520.43112 | 326000 | 1.69E-002 | 0.03366047 | 5.70E-004 | TRUE |
| N17 | 28.11 | 1115.53625 | 156800 | 7.11E-003 | 0.02946351 | 2.10E-004 | TRUE |
| N18 | 35.93 | 3.32262031 | 151000 | 2.20E-005 | 0.08961994 | 1.97E-006 | FALSE |
| N19 | 55 | 2.29891E-0 | 75400 | 3.05E-011 | 0 | 0.00E+001 | FALSE |
| N2 | [38.77] | 0 | 0 | NA | 0 | NA | NA |
| N20 | [37.94] | 0 | 25200 | 0.00E+001 | 0 | 0.00E+001 | FALSE |
| N21 | 32.03 | 60.4299199 | 94600 | 6.39E-004 | 0.15988723 | 1.02E-004 | TRUE |
| N22 | 32.68 | 37.2640569 | 232000 | 1.61E-004 | 0.04686605 | 7.53E-006 | FALSE |
| N23 | 31.86 | 68.5748911 | 216000 | 3.17E-004 | 0.01390508 | 4.41E-006 | FALSE |
| N24 | 33.53 | 19.8027085 | 202000 | 9.80E-005 | 0.12474298 | 1.22E-005 | FALSE |
| N25 | 55 | 2.29891E-0 | 163000 | 1.41E-011 | 0 | 0.00E+001 | FALSE |
| N26 | 28.05 | 1166.44639 | 184800 | 6.31E-003 | 0.01644869 | 1.04E-004 | TRUE |
| N27 | 55 | 2.29891E-0 | 304000 | 7.56E-012 | 0 | 0.00E+001 | FALSE |
| N28 | 27.5 | 1756.00132 | 1320000 | 1.33E-003 | 0.01922547 | 2.56E-005 | FALSE |
| N29 | 30.78 | 143.203366 | 60600 | 2.36E-003 | 0.01517688 | 3.59E-005 | FALSE |
| N3 | [30.13] | 0 | 470000 | 0.00E+001 | 0 | 0.00E+001 | FALSE |
| N30 | 36.67 | 1.91622802 | 37000 | 5.18E-005 | 0 | 0.00E+001 | FALSE |
| N4 | 28.61 | 1066.45345 | 578000 | 1.85E-003 | 0.03731838 | 6.89E-005 | FALSE |
| N5 | 31.16 | 193.079015 | 242000 | 7.98E-004 | 0.10249716 | 8.18E-005 | FALSE |
| N6 | 34.21 | 25.0033095 | 43400 | 5.76E-004 | 0.00310273 | 1.79E-006 | FALSE |
| N7 | 34.95 | 15.2269171 | 23200 | 6.56E-004 | 0.03400166 | 2.23E-005 | FALSE |

-continued

| Sample ID | Cp | pg DNA | pg Bis-DNA | rel Conc (pgDNA/ pgBisDNA) | Intensity Proportion | total Conc (Intensity Proportion* relConc) | C > 0.0001 Call |
|---|---|---|---|---|---|---|---|
| N8 | 33.13 | 51.5636816 | 240000 | 2.15E−004 | 0.36826225 | 7.91E−005 | FALSE |
| N9 | 55 | 2.22243E−0 | 47000 | 4.73E−010 | 0 | 0.00E+001 | FALSE |

SHORT DESCRIPTION OF THE FIGURES

FIG. 1 Calibration curve of the above described assay with $2^{nd}$ derivative method. Points are individual measurement values at respective spiked mDNA concentrations in 50 ng sperm background. Different colors symbolize independent dilutions of the spike mDNA. Black solid line gives median measurement value, black dotted lines give 90% confidence interval. Fat dotted line is the ideal calibration curve.

FIG. 2 Calibration curve of the above described F2 assay based on estimation of uniformly methylated DNA ($2^{nd}$ derivative method for primers, maximum intensity for intensity proportion). Points are individual measurement values at respective spiked mDNA concentrations in 50 ng sperm background. Different colours symbolize independent dilutions of the spike mDNA. Black solid line gives median measurement value, small dotted lines give 90% confidence interval. Fat dotted line is the ideal calibration curve.

FIG. 3 Amplification curves of TMEFF2 assay on 20 cancer samples. The triangles show amplification curve of artificial methylation control (100 ng SSS1 treated DNA). The diamonds show amplification curve of negative water control.

FIG. 4 Logarithmic amplification curves of TMEFF2 assay on 20 cancer samples. The triangles show amplification curve of artificial methylation control (100 ng SSS1 treated DNA). The diamonds show amplification curve of negative water control.

The invention claimed is:

1. A method for the quantification of uniformly methylated cytosines in DNA, said method comprising:
   a) chemically treating a genomic DNA sample in such a way that all of the unmethylated cytosine bases are converted to uracil or another base which is dissimilar to cytosine in terms of base pairing behaviour, while the 5-methylcytosine bases remain unchanged,
   b) amplifying the chemically pretreated DNA in a real time PCR using at least one methylation specific probe and one methylation specific primer or blocker,
   c) determining the amount of DNA methylated at the primer/blocker binding site and the proportion of DNA methylated at the probe binding site within the amplificate,
   d) calculating the amount of uniformly methylated DNA using the values obtained in step c.

2. A method according to claim 1, wherein bodily fluids are analysed.

3. A method according to claim 1, wherein the methylation specific probe in step b is a hybridization or hydrolysis probe.

4. A method according to claim 1, wherein in step c) the amount of methylated DNA at the primer/blocker binding site is determined by a criteria derived from a shape of a real time curve.

5. A method according to claim 4, wherein the criteria is a ct value.

6. A method according to claim 5, wherein the ct value is derived from a higher order derivative of an amplification curve.

7. A method according to claim 6, wherein the ct value is calculated according to a second derivative maximum method.

8. A method according to claim 1, wherein the amount of methylated DNA at the primer/blocker binding site is calculated by fitting a parametric model to an amplification curve.

9. A method according to claim 8, wherein a hydrolysis probe is used and a sigmoid function serves as a model.

10. A method according to claim 8, wherein the parametric model used is described by the formula: $f = y_0 + a/(1+\exp((x_0-x)/b))$, wherein $y_0$ is base fluorescence, a is the difference between $y_0$ and maximum fluorescence, x is actual cycle number, $x_0$ is the inflection point (first derivative maximum) and b is a parameter for slope of the curve.

11. A method according to claim 1, wherein in step c) the proportion of cytosine positions methylated at the probe binding site in the amplificate is determined by a criteria derived from a signal intensity.

12. A method according to claim 1, wherein the proportion of cytosine positions methylated at the probe binding site in the amplificate is determined by a linear interpolation between fluorescence intensities from negative controls and from a standard sample.

13. A method according to claim 1, wherein the proportion of cytosine positions methylated at the probe binding site in the amplificate is determined by a global calibration of maximum and/or minimum intensity over several samples.

14. A method according to claim 12, wherein the proportion is calculated by the formula: $p = (y-y_0)/(y_1-y_0)$, wherein y is intensity of the analyzed sample, $y_0$ is intensity of the negative control and $y_1$ is intensity of the standard sample.

15. A method according to claim 1, wherein the proportion of cytosine positions methylated at the probe binding site in the amplificate is determined by using an additional probe that is specific for non-methylation.

16. A method according to claim 15, wherein the proportion is calculated by the formula: $p = y_{CG}/(y_{CG}+y_{TG})$, wherein $y_{CG}$ is fluorescence intensity of the methylation specific probe and $y_{TG}$ is fluorescence intensity of the non-methylation specific probe.

17. A method according to claim 14, wherein y, $y_0$, $y_1$ or $y_{CG}$, $y_{TG}$ as defined in claim 14 are computed as the maximum intensities of respective amplification curves.

18. A method according to claim 1, wherein y, $y_0$, $y_1$ or $y_{CG}$, $y_{TG}$ are computed as intensities in a cycle where a second derivative of a respective amplification curve is zero (inflection point).

19. A method according to claim 10, wherein y, $y_0$, $y_1$ or $y_{CG}$, $y_{TG}$ are computed by using parameter a from the model according to claim 10.

20. A method according to claim 1, wherein in step d) the amount of uniformly methylated DNA $C_u$ is calculated by the product of the proportion of amplificates methylated at the probe p and the concentration of amplificates methylated at the primer/blocker ($C_p$): $C_u = p*C_p$.

21. A method according to claim 1, wherein in step c) the amount of cytosine positions methylated at the primer/blocker binding site is determined by the second derivative maximum method and the proportion of cytosine positions methylated at the probe binding site in the amplificate is determined by using negative control and standard samples to linearly interpolate between minimum and maximum intensity.

* * * * *